(12) United States Patent
Dodd et al.

(10) Patent No.: US 6,649,626 B1
(45) Date of Patent: Nov. 18, 2003

(54) N-SUBSTITUTED 1-(LACTONE) ISOQUINOLONES FOR TREATING NERVOUS DISORDERS

(75) Inventors: Robert Dodd, Paris (FR); Rodolphe Razet, Charenton-le-Pont (FR); Pierre Jean-Paul Potier, Paris (FR); Werner Sieghart, Vienna (AT); Frantisek Jursky, Bratislava (SK); Roman Furtmuller, Pyra (AT); Erwin Sigel, Bremgarten (CH); Urs Thomet, Hofstetten (CH)

(73) Assignees: Centre National de la Recherche Scientifique (CNRS), Paris (FR); Universite de Bern, Bern (CH); Innovationsagentur GmbH, Vienna (AT)

( * ) Notice: Subject to any disclaimer, the term of this patent is extended or adjusted under 35 U.S.C. 154(b) by 0 days.

(21) Appl. No.: 10/111,081

(22) PCT Filed: Oct. 20, 2000

(86) PCT No.: PCT/FR00/02927
§ 371 (c)(1),
(2), (4) Date: Aug. 15, 2002

(87) PCT Pub. No.: WO01/29030
PCT Pub. Date: Apr. 26, 2001

(30) Foreign Application Priority Data

Oct. 22, 1999 (FR) .............................. 99 13232

(51) Int. Cl.⁷ .................. A61K 31/4725; C02D 405/04
(52) U.S. Cl. ...................... 514/309; 546/141; 546/139; 546/89; 514/307; 514/291
(58) Field of Search ................ 514/309, 307, 514/291; 546/141, 139, 89

(56) References Cited

FOREIGN PATENT DOCUMENTS

EP 0 419 247 3/1991
FR 2 750 427 1/1998

OTHER PUBLICATIONS

Razet, R. et al. : 5–[1'–(2'–N–Arylsulfonyl–1',2',3',4'–tetrahydroisoquinolyl)]–4,5–dihydro–2(3H)–furanones: Positive allosteric modulators of the GABA–A receptor with a new mode of action. J. Med. Chem. vol. 43, pp. 4363–4366, 2000.

M.C.W. Minchin et al., "A Novel GABA$_A$–Like Autoreceptor Modulates GABA Release", Chemical Abstracts, vol. 117, No. 21, Abstract No. 117:205616m, (Nov. 23, 1992).

P. Krogsgaard–Larsen et al., "GABA$_A$ Receptor Agonists, Partial Agonists, and Antagonists. Design and Therapeutic Prospects", Journal of Medicinal Chemistry, vol. 37, No. 16, pp. 2489–2505, (Aug. 5, 1994).

Wu et al., "Synthesis and Biological Evaluation of Non–Peptide Cyclophilin Ligands," J. Med. Chem., 46:1112–1115 (2003).

Wauquier et al.; Loreclezole (R72 063): An anticonvulsant chemically unrelated to prototype antiepileptic drugs; Drug Dev. Res. 19:375–292 (1990).

Richard Manske; The alkaloids of fumaraceous plants II Dicentra cucullaria, Canadian Journal of Research, 265–269.

Study et al.; Diazepam and (–)–pentobarbital Fluctuation analysis reveals different mechanisms for potentiation of γ–aminobutyric acid responses in cultured central neurons; Proc. Natl. Acad. Sci. USA, 78(11) 7180–7184 (1981).

Werner Sieghart; Structure and pharmacology of γ–aminobutyric acid$_A$ receptor subtypes; Pharmacological Reviews 47(2) 181–234 (1995).

Sieghart et al.; Affinity of various ligands for benzodiazepine receptors in rat cerebellum and hippocampus; Biochem. Pharmacol. 33(24) 4033–4038 (1984).

Sigel et al.' The effect of subunit composition of rat brain GABA$_A$ receptors on channel function; Neuron 5:703–711 (1990).

Erwin Sigel; J. Physiol.; Properties of single sodium, channels translated by xenopus oocytes after injection with messenger ribonucleic acid; 386:73–90 (1987).

Kardos et al.; Synthesis, anti–GABA activity and preferred conformation of bicuculline and norbicuculline enantiomers; Eur. J. Med. Chem. 31:761–765 (1996).

(List continued on next page.)

Primary Examiner—C. S. Aulakh
(74) Attorney, Agent, or Firm—Finnegan, Henderson, Farabow, Garrett & Dunner, LLP

(57) ABSTRACT

The invention concerns compounds of general formula (I) wherein: Z represents a sulphur or oxygen atom, NH, N-alkyl or Nboc; group R', identical or different, represent each a hydrogen atom, a OCH$_3$ group or a OCH$_2$O group; group R" represents a hydrogen or a CH$_3$ group; group X represents a carbonyl, sulphonyl or CO$_2$ group; and group R represents an alkyl, aryl, alkenyl or aralkyl group. The invention also concerns the preparation of said compounds, pharmaceutical compositions containing them and their use for stimulating γ-amino-butyric acid activity and as medicine for treating nervous disorders.

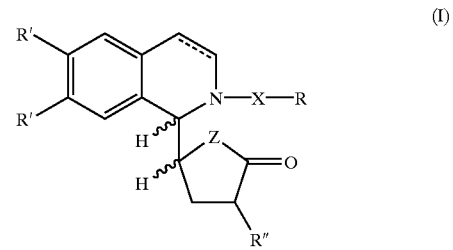

(I)

11 Claims, No Drawings

OTHER PUBLICATIONS

Allan et al.; Synthesis of substituted (+)–bicuculline derivatives through chloromethylation; Aust. J. Chem; 43:1259–68 (1990).

Rassu et al.; Expeditious Syntheses of sugar–modified nucleosides and collections thereof exploiting furan–, pyrrole–, and thiophene–based siloxy dienes; J. Med. Chem. 40:168–180 (1997).

Casiraghi et al.; N–(tert–butoxycarbonyl)–2–(tert–butyldimethylsiloxy)pyrrole: A promising compound for synthesis of chiral nonracemic hydroxylated pyrrolidine derivatives; J. Org. Chem.; 57:3760–3763 (1992).

Hillard et al.; Auxiliary silicon in regioselective cobalt catalyzed protoberberine syntheses; Tetrahedron, 39(6) 905–911 (1983).

Jefford et al.; A short route to furanosesquiterpenes using a new siloxyfuran building block. The synthesis of freelingnite and dehydrolasiosperman; Tetrahedron Letters, 31(40) 5741–5744 (1990).

Morimoto et al.; An efficient approach toward pyrrolidinyl–lactone system characteristic of the stemona alkaloids. Lewis acid catalyzed stereoselective reaction of n–benzyloxycarbonyl–2–methoxypyrrolidine with 3–methyl–2–trimethylsilyoxyfuran; Tetrahedron Letters 34(36) 5773–5776 (1993).

Kardos et al.; Inhibition of [$^3$H]GABA binding to rat brain synaptic membranes by bicuculline related alkaloids; Biochem. Pharmacol. 33(22) 3537–3545 (1984).

M.A. Simmonds; Presynaptic actions of γ–aminobutyric acid and some antagonists in a slice preparation of cuneate nucleus; Br. J. Pharmac. 63:495–502 (1978).

Bhattacharyya et al.; Studies on the bicuculline–GABA interactions on neuronal membrane with fluroescent labeled anti–bicuculline antibodies; Indian J. of Biochem. & Biophysics 18:171–176 (1981).

Casiraghi et al.; The four–carbon elongation of *aldehydo* sugars using 2–(trimethylsiloxy)furan: A butenolide route to higher monosaccharides; Journal of Organic Chemistry 55(9) 2565–2567 (1990).

Zezula et al.; Interaction of allosteric ligands with $GABA_A$ receptors containing one, two, or three different subunits; European Journal of Pharmacology 301:207–214 (1996).

Gardner et al.; The rapidly expanding range of neuronal benzodiazepine receptor ligands; Progress in Neurobiology 40:1–61 (1993).

Whaley et al.; The synthesis and resolution of (±)–corlumine; 1067–1070.

Arbilla et al.; Pharmacological profile of the imidazopyridine zolpidem at benzodiazepine receptors and electrocorticogram in rats; Naunyn–Schmiedeberg's Arch Pharmacol 330:248–251 (1985).

N-SUBSTITUTED 1-(LACTONE) ISOQUINOLONES FOR TREATING NERVOUS DISORDERS

This application is a 371 of PCT/FR00/02927 filed Oct. 20, 2000, now WO 01/29030 Sep. 26, 2001.

The present invention relates to N-substituted 1-(2-butyrolactones and 2-thiobutyrolactones)-isoquinolines, their preparation, pharmaceutical compositions containing them and their use as stimulant of γ-aminobutyric acid activity and as medicament preferably intended for treating nervous disorders.

γ-aminobutyric acid (or GABA (I)) is the most important inhibiting neurotransmitter of the central nervous system. It acts at the level of three distinct classes of receptors called GABA-A, GABA-B and GABA-C receptors. The GABA-A receptor, whose amino acid sequence has been determined by cloning techniques is a pentameric structure composed of α, β, γ, δ and/or ρ subunits. So far, 6 α subunits, 3 β subunits, 3 γ subunits, 1 δ subunit and 2 ρ subunits have been identified and sequenced. Five of these subunits (for example $2\alpha_1$ $2\beta_2$ $\gamma_2$) assemble to form a channel which is permeable to chloride ions. By binding to this GABA-A receptor, GABA increases the permeability of the channel to chloride ions, thus inhibiting neuronal transmission. In the light of the large number of possible permutations of the various subunits, a very high heterogeneity of the GABA-A receptor is observed in the brain of mammals and various structures of the brain generally show a preponderance for certain combinations of subunits.

The search for ligands selective for one of these various subunits of GABA-A receptors is a major objective of clinical medical research in this field.

Apart from GABA, a large number of various classes of compounds are known which bind to the GABA-A receptor. Some products, such as muscimol and isoguvacine, bind directly to the same site as GABA on the GABA-A receptor and stimulate the receptor in the same manner as GABA itself. Unlike these agonists, some substances, such as bicuculline (2), competitively inhibit the action of GABA. Such antagonists of the GABA receptor show convulsant properties in vivo (P. Krogsgaard-Larsen, B. Frolund, F. S. Jorgensen, A. Schousboe, J. Med. Chem., 1994, 37, 2489).

The inhibitory action of GABA may be modulated by compounds which interact with a variety of allosteric sites on the GABA-A receptor which are distinct from the GABA recognition site. One of the best known classes of allosteric modulators of the GABA-A receptor is that of the benzodiazepines (for example diazepam (3)). By thus binding to their own recognition site on the GABA-A receptor (the benzodiazepine receptor or BZR), these compounds improve the action of GABA by increasing the frequency of opening of the chloride channel (R. E. Study, J. L. Barker, Proc. Natl. Acad. Sci. USA, 1981, 78, 7180). This results in the anticonvulsant, anxiolytic, sedative-hypnotic and muscle-relaxing activities of these products which are widely used in the clinical field. Other classes of compounds which are structurally unrelated to the benzodiazepines, such as triazolopyridazines (for example Cl 218872 (4)), imidazopyridines (for example zolpidem (5)), cyclopyrrolones (for example zopicolone (6)) and β-carbolines (for example β-CCM (7)), can also bind to the benzodiazepine receptors. In the case of the latter, certain derivatives inhibit, rather than increase, the neuroinhibitory action of GABA (R. L. Macdonald, R. E. Twyman in "Ion Channels" ed. by T. Narahashi, Vol. 3, pp. 315–343, Plenum Press, New York, 1992). In this case, the compounds, which are generally convulsant, are called inverse agonists (or negative allosteric modulators) of BZR, to distinguish them from agonists (or positive allosteric modulators) of BZR which are therapeutically useful. Some of these products demonstrate selectivity on various subclasses of GABA-A/benzodiazepine receptors. Thus, zolpidem, which is clinically used as a hypnotic, is selective for the subclass of benzodiazepine receptors which are predominantly found in the cerebellum (BZ1 receptors) (S. Arbilla, H. Depoortere, P. George, S. Z. Langer, Naunyn-Schmiedeberg's Arch. Pharmacol., 1985, 330, 248). This selectivity results in a narrower activity spectrum (for example anxiolysis without hypnotic effect) or in a reduction in the undesirable effects of this type of product (addiction, dependence, amnesia and the like).

Other sites exist on the GABA-A receptor which also make it possible, depending on its binding with an appropriate molecule, to modulate the activity of GABA. Among these sites, there may be mentioned those for neurosteroids (for example 3α-OH-5α-pregnan-20-one), barbiturates (for example pentobarbital), anesthetics (for example propofol), cage convulsants t-butyl-bicyclophosphorothionate which bind to the picrotoxin site of the GABA-A receptor (W. Sieghart, Pharmacol. Rev., 1995, 47, 181 and C. R. Gardner, W. R. Tully, C. J. R. Fiedgecock, Prog. Neurobiol., 1993, 40, 1). Other binding sites, which are less well characterized but which are apparently distinct, are those for loreclezole and γ-butyrolactones. Such compounds also positively modulate the action of GABA and this effect results in an anticonvulsant and/or anxiolytic action in vivo.

It is thus clear that a large number of allosteric modulatory sites, which can increase the action of GABA and thus demonstrate a therapeutic efficacy in a wide range of central nervous system disorders, exist on the GABA-A receptor. It can thus be reasonably concluded that novel chemical structures can discover other allosteric modulatory sites not yet characterized on the GABA-A receptor or bind to known sites with higher affinities or higher selectivities. Such compounds may, as a result, demonstrate a potent and/or highly specific activity as well as lower undesirable side effects in the treatment of such disorders.

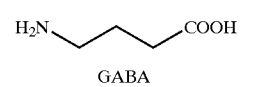

GABA

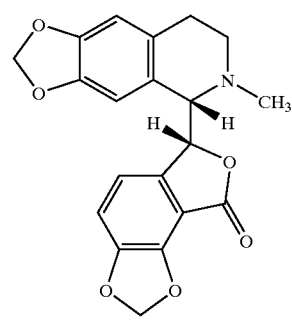

bicuculline

-continued

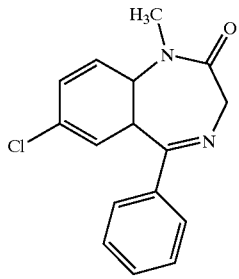

Diazepam

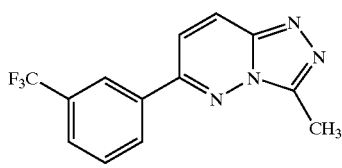

CI 218872

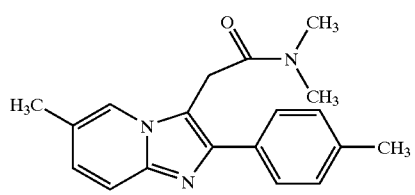

STILNOX® (zolpidem)

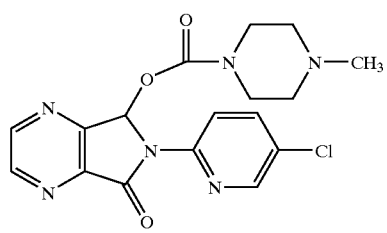

IMOVANE® (zopiclone)

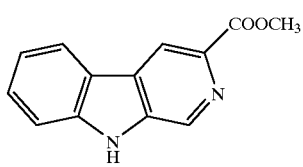

β-CCM

Wyeth laboratories claim that compound 17, which is obtained according to scheme 1 (and related compounds) are antagonists of the GABA autoreceptor and are thus useful for the treatment of central nervous system disorders and of pain (European patent No. EP0419247A2). The GABA autoreceptor is considered as being a pharmacological entity distinct from the GABA-A receptor itself. Type 17 compounds thus have no action or have a very weak action on GABA-A receptors. The GABA autoreceptor ligands exhibit different structural requirements from those of the GABA-A receptor.

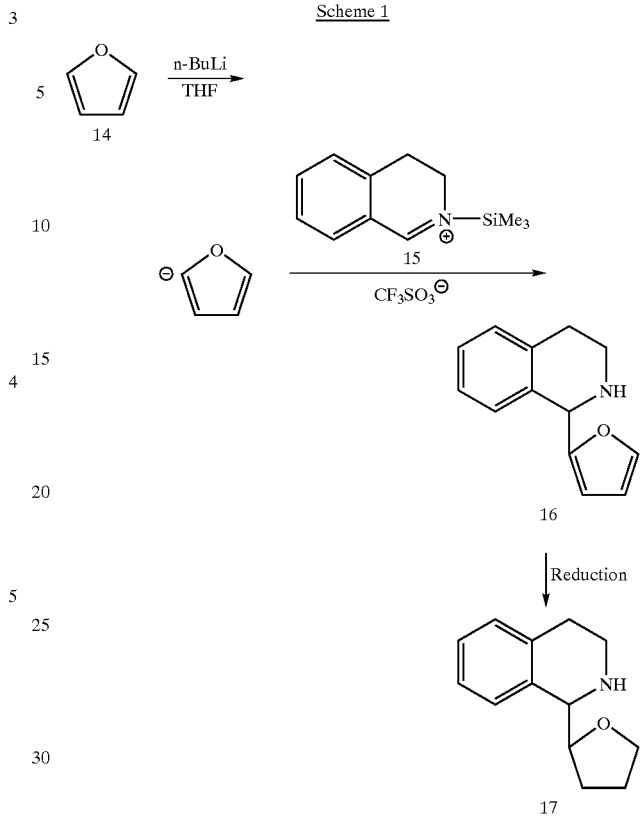

Bicuculline 2, whose molecular structure has been used as the starting point for designing the compounds of the present invention, is a natural product which was isolated from Dicentra cucullaria in 1932 by Manske (R. H. Manske, Can. J. Res., 1932, 7, 265). This compound, a potent convulsant, is a competitive antagonist of the GABA-A receptor which binds to the same site as GABA itself (M. A. Simmonds, Br. J. Pharmacol., 1978, 63, 495). Because of the convulsant nature of bicuculline, very few structure-function studies have been carried out on this molecule. Allan and Apostopoulos (R. D. Allan, C. Apostopoulos, Aust. J. Chem., 1990, 43, 1259) have described the preparation of bicuculline derivatives modified at the C-9 position starting from 9-hydroxymethylbicuculline whose synthesis has been described by Bhattacharyya et al. (A. Bhattacharyya, K. M. Madyastha, P. K. Bhattacharyya, M. S. Devanandan, Indian J. Biochem. Biophys., 1981, 18, 171). No biological data has been reported. Simonyi et al. (J. Kardos, G. Blasko, P. Kerekes, I. Kovacs, M. Simonyi, Biochem. Pharmacol., 1984, 33, 3537) have determined the GABA-A receptor activities of 45 phthalideisoquinoline alkaloids related to (+)-bicuculline. No compound was more active than bicuculline, but in all cases, the erythro stereoisomer (that is to say that of bicuculline) was more active than the threo isomer. This conclusion was confirmed by the same authors in related studies published in 1996 (J. Kardos, T. Blandl, N. D. Luyen, G. Dornyei, E. Gacs-Baitz, M. Simonyi, D. J. Cash, G. Blasko, C. Szantay, Eur. J. Med. Chem., 1996, 31, 761). The importance of the fused ring "A" of bicuculline for the GABA-A receptor activity has never been demonstrated, except in the present invention. While bicuculline was the starting point of our study, the most active molecules synthesized are considerably different from bicuculline in that:

the fused ring "A" is absent and the 3,4 bonds are saturated, the threo rather than erythro isomers are the most active, the aromatic benzo ring of the isoquinoline entity is not substituted, the nitrogen atom of the isoquinoline entity is substituted with an aryl carbamate, an aryl sulfonate rather than a methyl group.

Finally, the compounds of the present invention bind at best only weakly to the GABA site on the GABA-A receptor (thus measured by $H^3$-muscimol displacement studies) but rather bind to the benzodiazepine sites of the GABA-A receptor or to an as yet unidentified site of this receptor or, in some cases, to the latter two sites. More importantly, whereas bicuculline and these known analogs inhibit the currents produced by GABA in the neurons (giving rise to their pharmacological convulsant profile in vivo), the compounds of the present invention strongly stimulate the currents produced by GABA in the same manner as the therapeutically useful benzodiazepines.

The present invention therefore relates to the compounds of general formula:

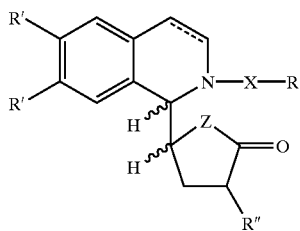

in which:
Z represents a sulfur atom, an oxygen atom, NH, N-alkyl or Nboc,
the groups R', which may be identical or different from one another, each represent a hydrogen atom, an $OCH_3$ group or an $OCH_2O$ group,
the group R" represents a hydrogen or a $CH_3$ group,
the group X represents a carbonyl, sulfonyl or $CO_2$ group
and he group R represents an alkyl, aryl, alkenyl or aralkyl group
it being possible for these compounds to exist in the form of a racemic mixture or in an optically pure form.

A preferred group of compounds according to the invention consists of the compounds for which Z is an oxygen atom or NbOc. The compounds of the present invention for which Z is an oxygen atom are particularly preferred because of their high activity.

A particular group of compounds according to the invention consists of the compounds of general formula:

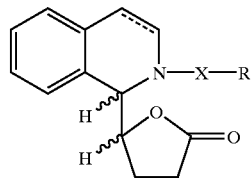

in which:
the group X represents a carbonyl, sulfonyl or $CO_2$ group,
and the group R represents an alkyl, aryl, alkenyl or aralkyl group.

Among the preferred compounds of the invention, there may be mentioned the compound of formula:

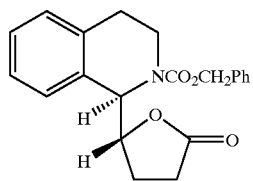

and that of formula:

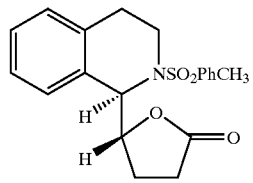

The term alkyl group is understood to mean the linear or branched, substituted or unsubstituted alkyl groups having from 1 to 4 carbon atoms. Preferred examples of alkyl groups are the $CH_3$ and $C_2H_5$ groups.

The term alkenyl group is understood to mean the linear or branched, substituted or unsubstituted alkenyl groups having from 1 to 4 carbon atoms.

The term aryl groups is understood to mean substituted or unsubstituted aromatic rings having from 5 to 8 carbon atoms, having one or more aromatic rings. The aromatic rings may be joined or fused. Examples of preferred aromatic rings are phenyls and naphthyls. Examples of preferred substituents of these rings are alkyl groups such as $CH_3$, halogen atoms such as Cl, halogenated alkyl groups such as $CF_3$ or groups of the $OCH_3$ type.

The term aralkyl groups is understood to mean aryl groups, as defined above, linked to the sulfonyl or carbonyl or $CO_2$ group via an alkyl group as defined above. A preferred example of an aralkyl group is the $CH_2Ph$ group.

All the compounds according to the invention possess an asymmetric center and can therefore exist in the form of optical isomers. The present invention comprises these isomers either separately or as a mixture.

The present invention also relates to the method of preparing these compounds which may be the following: the compound of general formula:

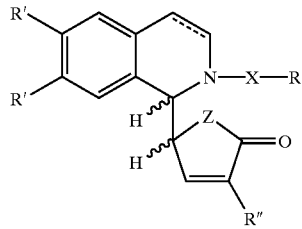

in which:
Z represents a sulfur atom, an oxygen atom, NH, N-alkyl or Nboc, preferably an oxygen atom,
the groups R', which may be identical or different from one another, each represent a hydrogen atom, an $OCH_3$ group or an $OCH_2O$ group,
the group R" represents a hydrogen or a $CH_3$ group,
the group X represents a carbonyl, sulfonyl or $CO_2$ group
and the group R represents an alkyl, aryl, alkenyl or aralkyl group, is selectively hydrogenated with $H_2$ in the presence of Pd—C to give the compounds according to the present invention.

This method may comprise a preliminary step of condensing, in the presence of an acylating or sulfonylating agent, a silyl enol ether represented by the general formula:

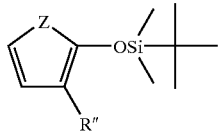

in which:
Z represents a sulfur atom, an oxygen atom, NH, N-alkyl or Nboc, preferably an oxygen atom,
and R" represents a hydrogen atom or a $CH_3$ with a salt of 3,4-dihydroisoquinoline represented by the following general formula:

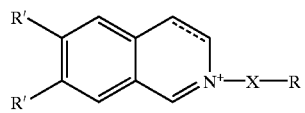

in which:
the groups R', which may be identical or different from one another, each represent a hydrogen atom, an $OCH_3$ group or an $OCH_2O$ group,
the group X represents a carbonyl, sulfonyl or $CO_2$ group
and the group R represents an alkyl, aryl, alkenyl or aralkyl group.

The present invention also relates to pharmaceutical compositions comprising, as active ingredient, one of the compounds defined above and an appropriate excipient. These compositions may be formulated for administration to mammals, including humans. The dosage varies according to the treatment and according to the condition in question. These compositions are produced so as to be administrable by the digestive or parenteral route.

In the pharmaceutical compositions of the present invention for oral, sublingual, subcutaneous, intramuscular, intravenous, transdermal, local or rectal administration, the active ingredient may be administered in unit forms for administration, as a mixture with conventional pharmaceutical carriers, to animals or to human beings. The appropriate unit forms for administration comprise the forms for oral administration such as tablets, gelatin capsules, powders, granules and oral solutions or suspensions, forms for sublingual and buccal administration, forms for subcutaneous, intramuscular, intravenous, intranasal or intraocular administration and forms for rectal administration.

When a solid composition is prepared in the form of tablets, the principle active ingredient is mixed with a pharmaceutical vehicle such as gelatin, starch, lactose, magnesium stearate, talc, gum arabic and the like. The tablets may be coated with sucrose or other appropriate materials or alternatively they may be treated such that they have a prolonged or delayed activity and such that they continuously release a predetermined quantity of active ingredient.

A preparation as gelatin capsules is obtained by mixing the active ingredient with a diluent and pouring the mixture obtained into soft or hard gelatin capsules.

A preparation in the form of a syrup or elixir may contain the active ingredient together with a sweetener, an antiseptic, as well as a flavoring agent and an appropriate coloring agent.

The water-dispersible powders or granules may contain the active ingredient as a mixture with dispersing agents or wetting agents, or suspending agents, as well as with flavor correctors or sweeteners.

For rectal administration, suppositories are used which are prepared with binders which melt at rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersing agents and/or wetting agents.

The active ingredient may also be formulated in the form of microcapsules, optionally with one or more carrier additives.

The present invention also relates to the use of these compounds as stimulant of the activity of γ-aminobutyric acid acting via the GABA-A receptor of the central nervous system.

The compounds according to the invention and the pharmaceutical compositions comprising them may be used as a medicament, in particular for the treatment of nervous disorders. These disorders are preferably of the type including epilepsy, anxiety, depression, sleep and memory disorders, panic attacks, muscle contractions, pain, dependence on alcohol or on benzodlazepines or psychotic behavior.

SYNTHESIS

The active compounds of the present invention (that is to say having the general structure 8) may all be prepared by the same method (scheme 2). Briefly, the substituted or unsubstituted derivatives of 3,4-dihydroisoquinoline 11 (which are prepared according to published methods: R. L. Hillard, C. A. Parnell, K. P. C. Vollhardt, Tetrahedron, 1983, 39, 905 and W. M. Whaley, M. Meadow, J. Chem. Soc., 1953, 1067) react first of all in acetonitrile at 0° C. with an aromatic acid chloride or an aryl chloroformate or an arylsulfonyl chloride for 15 to 30 min. The reaction mixture is then treated with a dienolic silyl ether 10 (prepared by reacting commercial butyrolactone 9 with trialkylsilyl triflates according to published methods: (a) G. Casiraghi, L. Colombo, G. Rassu, R. Spanu, J. Org. Chem., 1990, 55, 2565, (b) Y. Morimoto, K. Nishida, Y. Hayashi, H. Shirahama, Tet. Lett., 1993, 34, 5773, (c) G. Casiraghi, G. Rassu, P. Spanu, L. Pinna, J. Org. Chem., 1992, 57, 3760, and (d) C. W. Jefford, A. W. Sledeski. J-C Rossier, J. Boukouvalas, Tet. Lett., 1990., 31, 5741). After 15 to 30 minutes, the reaction mixture is treated in order to give the unsaturated coupled product 12 in the form of a mixture of 4 isomers. The double bond of compound 12 is reduced by catalytic hydrogenation on palladium on carbon in ethanol to give the compounds having the general structure 8. The two diastereoisomers of 8 (erythro-8 and threo-8) may be separated by either a) silica gel chromatography, or b) fractional crystallization, or c) HPLC on a silica column. In the cases where, in compound 8, Z=N-Boc, the treatment with trifluoroacetic acid in dichloromethane gives the deprotected compound 8 (Z=NH).

Scheme 2

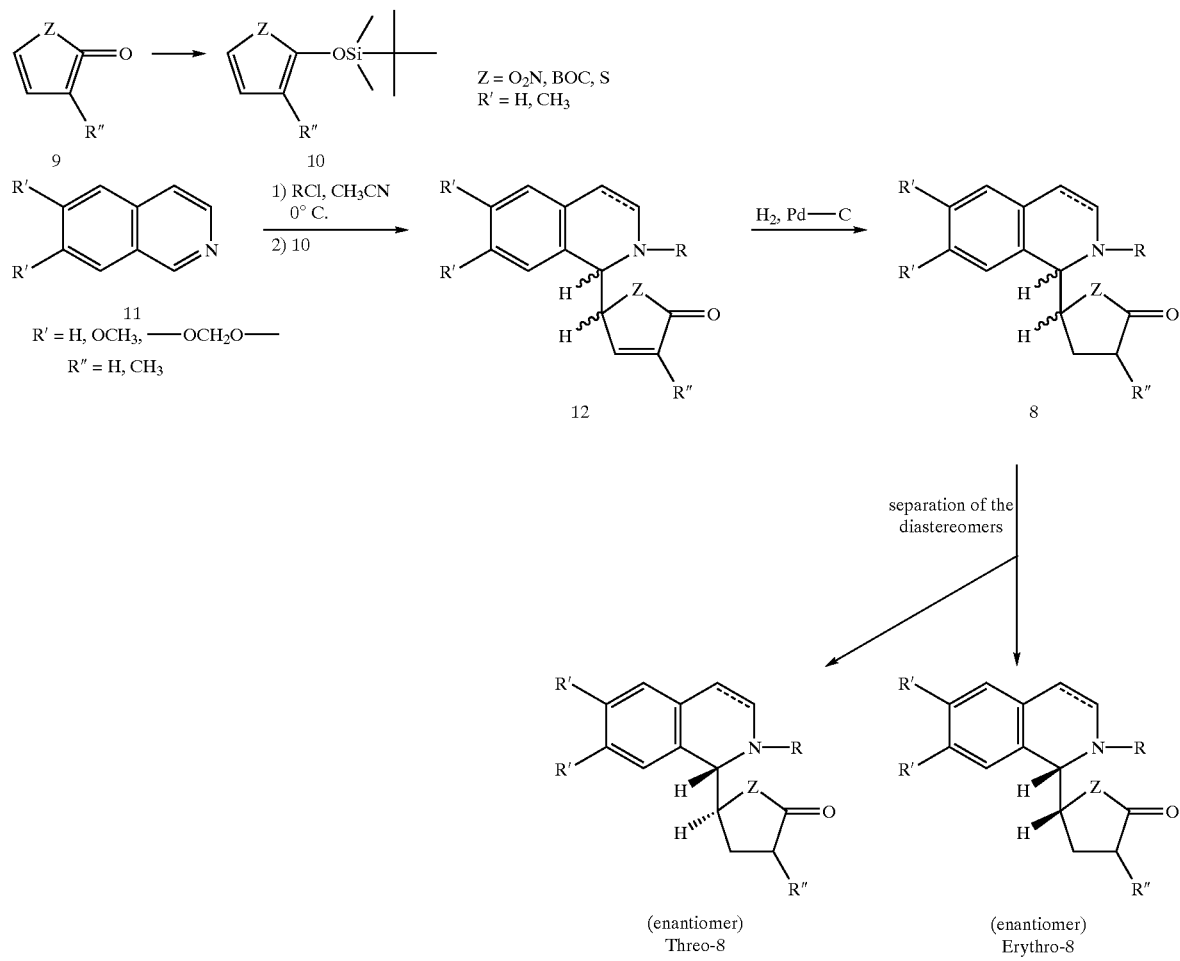

In the special case where the group "R" of compound 12 is a benzyloxycarbonyl group ("Cbz"), then the erythro and threo isomers may be separated by silica gel chromatography. Catalytic hydrogenation of the compound threo-12 (the most active isomer) over palladium on carbon simultaneously leads to the reduction of the double bond and to the elimination of the Cbz group to give the compound threo-13. The reaction of the latter with an aromatic acid chloride or an aryl chloroformate or an arylsulfonyl chloride in the presence of triethylamine may then give the desired compound threo-8. The advantage of this second method (scheme 3) for preparing the compound threo-8 (or erythro-8) consists in the fact that it only requires a separation of the diastereoisomers of compound 12 ($R=CO_2CH_2Ph$) whereas in the first method, the diastereoisomers of each final product 8 should be separated (sometimes with difficulty).

Scheme 3

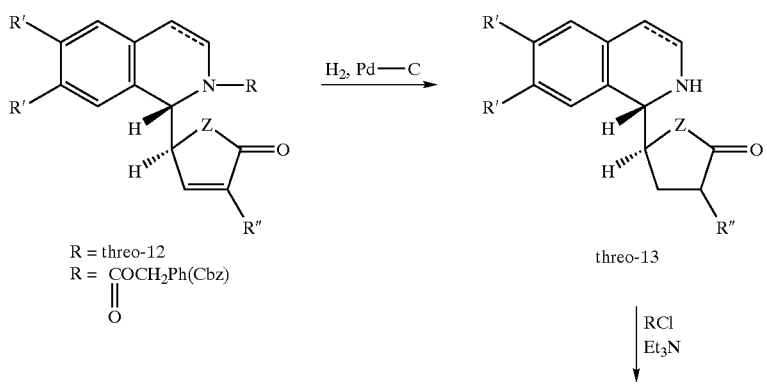

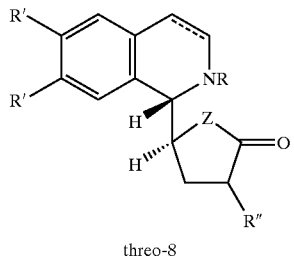

threo-8

Finally, given that the erythro-8 and threo-8 compounds are always in a mixture of enantiomers, the latter may be suitably separated by HPLC on a column with a chiral support.

STUDIES OF BINDING TO THE RECEPTOR

The compounds synthesized are tested in vitro for their capacity to bind to various sites on the GABA-A receptor, including the site for GABA itself (by $H^3$-muscimol displacement studies), the site for benzodiazepines (by displacement of $H^3$-flunitrazepam), the site for picrotoxin (by displacement of $^{35}S$-TBPS). Briefly, frozen membranes obtained from cerebellum or cerebellum-free brain are thawed, centrifuged and resuspended in 50 mM Tris-citrate buffer, pH 7.4, at a protein concentration of about 1 mg/ml. The membranes (0.5 ml) are then incubated in a total of 1 ml of solution containing 50 mM Tris-citrate buffer, pH 7.4, 150 mM NaCl and 2 nM [$^3$H]flunitrazepam or 2 nM [$^3$H] muscimol in the absence or in the presence of varying concentrations of the compound to be studied or of 10 $\mu$M diazepam or of 10 $\mu$M GABA, for 90 min at 4° C., respectively. For the [$^{35}$S]TBPS binding, the membranes are incubated in a total of 1 ml of solution containing 50 mM Tris-citrate buffer, pH 7.4, 200 mM NaBr and 2 nM [$^{35}$S] TBPS in the absence or in the presence of varying concentrations of the compound to be studied or of 10 $\mu$M TBPS or picrotoxinin for 180 min at room temperature (W. Sieghart, A. Schuster, Biochem. Pharmacol., 1984, 33, 4033, and J. Zezula et al., Eur. J. Pharmacol., 1996, 301, 207).

The membranes are then filtered through Whatman GF/B filters. When the binding of [$^3$H]flunitrazepam or of [$^3$H] muscimol is studied, the filters are rinsed twice with 5 ml of a buffer solution of 50 mM ice-cold Tris-citrate. When the binding of [$^{35}$S]TBPS is studied, the filters are rinsed three times with 3.5 ml of this buffer solution. The filters are transferred into scintillation flasks and subjected to scintillation counting after adding 3.5 ml of scintillation fluid. The nonspecific binding, determined in the presence of 10 $\mu$M diazepam, 10 $\mu$M GABA or 10 $\mu$M TBPS, is subtracted from the total of the binding of [$^3$H]flunitrazepam, of [$^3$H] muscimol or of [$^{35}$S]TBPS, respectively, in order to obtain the specific binding.

ELECTROPHYSIOLOGICAL STUDIES

The compounds synthesized are also studied for their capacity Lo cause the opening of the GABA-A receptor channel or to allosterically modulate the currents caused by GABA. For this purpose, the recombinant GABA-A receptors are expressed in Xenopus oocytes. Briefly, the Xenopus laevis oocytes are prepared, injected, defolliculated and the currents are recorded in the manner described (E. Sigel, J. Physiol., 1987, 386, 73 and E. Sigel, R. Baur, G. Trube, H. Möhler, P. Malherbe, Neuron, 1990, 5, 703). The oocytes are injected with 50 nl of cRNA dissolved in 5 mM K-Hepes (pH 6.8). This solution contains the transcripts encoding the various subunits at a concentration of 10 nM for $\alpha_1$, 10 nM for $\beta_2$ and 50 nM for $\gamma_2$. The RNA transcripts are synthesized from linearized plasmids encoding he desired protein using the message machine kit (Ambion) according to the manufacturers' recommendation. A poly(A) tail of about 300 residues is added to the transcripts using the yeast poly(A) polymerase (USB or Amersham). The cRNA combinations are coprecipitated in ethanol and stored at −20° C. The transcripts are quantified on agarose gels after staining with Radiant Red RNA stain (Bio-Rad) by comparing the staining intensities with various quantities of molecular weight markers (RNA-Ladder, Gibco-BRL). The electrophysiological experiments are carried out by the two-electrode voltage clamp method at a holding potential of −80 mV. The medium contains 90 mM NaCl, 1 mM KCl, 1 mM $MgCl_2$, 1 mM $CaCl_2$ and 10 mM Na-Hepes (pH 7.4). GABA is applied for 20 s and a washing period of 4 min is allowed to ensure complete restoration of desensitization. The perfusion system is cleaned between applications of the compounds by washing with dimethyl sulfoxide in order to avoid contamination. The compounds are applied at a concentration of 100 microM in the absence of GABA to see if they can act as channel agonists. To study allosteric modulation, GABA is first of all applied alone and then in combination with either 0.1 microM or 100 microM of compounds.

PHARMACOLOGICAL RESULTS

The compounds synthesized are tested in vitro for their capacity to displace tritiated flunitrazepam ($^3$H-Flu, a ligated selective for the benzodiazepine-binding site of the GABA-A receptor), $^{35}$S-TBPS (selective for the picrotoxin-binding site) and tritiated muscimol (selective for the GABA-binding site). These compounds are also tested for their capacity to prevent or to stimulate the currents caused by GABA in the oocytes of frogs expressing the $\alpha_1\beta_2\gamma_2$ subtype of the GABA receptor.

The detailed results for examples of compounds are shown in tables 1a to 1i.

TABLE 1a

| Cp No. | Code No. | Structure | % stimulation of the GABA currents (100 μM) | Inhibition of the tritiated ligands | | Other activities |
|---|---|---|---|---|---|---|
| | | | | Flu (100 μM) | % TBPS (100 μM) | |
| 42* | ROD127 (65:35 mixture) | 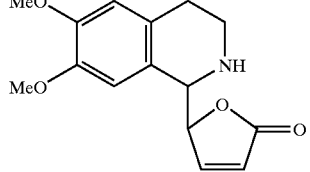 | −45 ± 6% (0.1 μM = 0%) | 30% (10 μM = 0%) | 0 | Displacement of muscimol 100 μM = 20% 10 μM = 0% |
| 27a* | CJ-52a / ROD.090B | 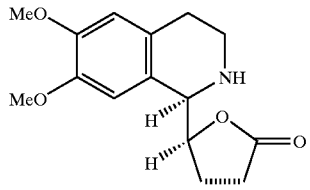 | 200 μM = 0% / 200 μM = 0% | −8% / 10% | 0% / negligible | |
| 27b* | ROD.090A | 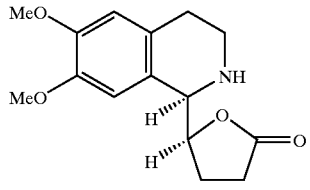 | 200 μM = −6% | negligible | negligible | |
| 28* | ROD.BIS1 | 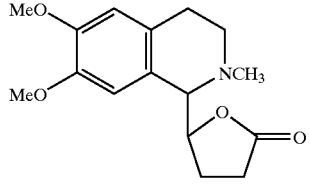 | 200 μM = +2% | 50 | 9% | Ro15-4513 displacement 100 μM = 50% |
| 30a* | ROD.07A | 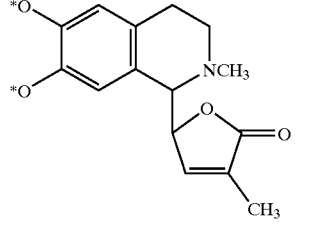 | −8% | negligible | 0% | |
| 30b* | ROD.07B | 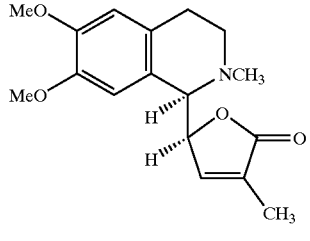 | −10% | negligible | 0% | |

The symbol * indicates a racemic mixture of enantiomers

TABLE 1b

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 43* | ROD173B | 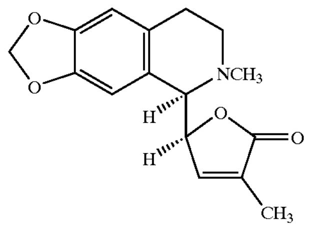 | −7 ± 2% | ~20% | 50% (10 μM = 10%) | Displacement of muscimol 100 μM = 50% 10 μM = 45% 0.5 μM = 30% |
| 31a* | ROD.056 | 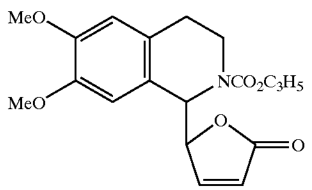 | +15% | negligible | 0 | |
| 31b* | ROD.058 (diast. mixture) | 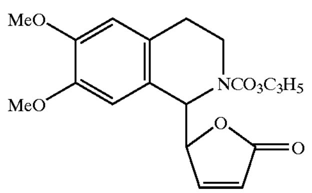 | +19% | negligible | negligible | |
| 32a* | ROD.059A / ROD.163B | 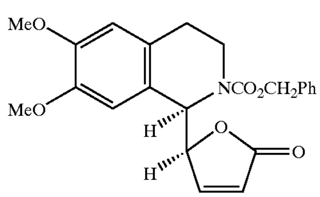 | +16% / +20 ± 7% | 40% / 15% (10 μM = ~10%) | 54% / 70% | Displacement of muscimol = 0% |
| 32b* | ROD.059B / ROD.163B | 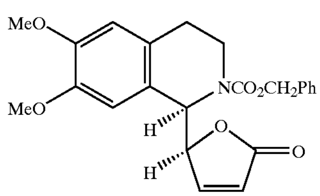 | +65% / +43 ± 8% | 50% / 50% (10 μM = 20%) | precipitation / 65% (10 μM = 10%) | Displacement of muscimol = 0% |
| 44* | ROD.166A | 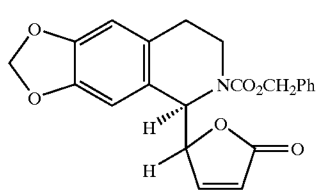 | 50 μM = +215 ± 16% 0.1 μM = 0% | 45% 10 μM = 20% 0.5 μM = <5% | 25% 10 μM = 25% 0.5 μM = 0% | Displacement of muscimol 100 μM = 10% stimulation 10 μM = 0% 0.5 μM = 10% |

The symbol * indicates a racemic mixture of enantiomers

TABLE 1c

| Cp No. | Code No. | Structure | % stimulation of the GABA currents (100 μM) | Inhibition of the tritiated ligands | | Other activities Displacement of Muscimol |
|---|---|---|---|---|---|---|
| | | | | % Flu (100 μM) | % TBPS (100 μM) | |
| 45* | ROD.166B | [structure: methylenedioxy-tetrahydroisoquinoline with NCO₃CH₂Ph and butenolide] | 50 μM = +128 ± 36% 0.1 μM = 0% | 45% 10 μM = 25% 0.5 μM = 0% | 40% 10 μM = 20% 0.5 μM = 0% | 100 μM = 20% 10 μM = 40% stimulation 0.5 μM = 0% |
| 46* | ROD.169A | [structure: 6,7-dimethoxy-tetrahydroisoquinoline with NCO₂CH₂Ph and methyl-butyrolactone] | 24 ± 5% (0.1 = 0%) | 0% | 0% | 100 μM = 0% |
| 47* | ROD.169B | [structure: 6,7-dimethoxy-tetrahydroisoquinoline with NCO₂CH₂Ph and methyl-butenolide] | 60 ± 26% (0.1 = 0%) | 10% | 0% | 100 μM = 0% |
| 48* | ROD.170A | [structure: 6,7-dimethoxy-tetrahydroisoquinoline with NCO₂CH₂Ph and butyrolactone] | +159 ± 31% (0.1 μM = 0%) | 35% | 60% (10 μM = 0%) | 100 μM = 0% |
| 49* | ROD.170B | [structure: 6,7-dimethoxy-tetrahydroisoquinoline with NCO₂CH₂Ph and butyrolactone] | +67 ± 9% (0.1 μM = 0%) | 30% | 45% (10 μM = 0%) | 100 μM = 0% |
| 50* | ROD.164A | [structure: tetrahydroisoquinoline with NCO₂CH₂Ph and butenolide] | +281 ± 35% 0.1 μM = +26 ± 6% (completely blocked by flumazenil) | 100% 10 μM = 90% 0.5 μM = 55% | 85% 10 μM = 30% 0.5 μM = 5% | 100 μM = 0% |
| 51* | ROD.164B | [structure: tetrahydroisoquinoline with NCO₂CH₂Ph and butenolide] | +225 ± 68% 0.1 μM = 0% | 85% 10 μM = 50% 0.5 μM = 0% | 90% 10 μM = 20% 0.5 μM = 0% | 100 μM = 0% |

The symbol * indicates a racemic mixture of enantiomers

TABLE 1d

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 52* | ROD.213A (+~5% 213B) | [structure] | N.T. | IC$_{50}$ = 8 μM (cerebellum) IC$_{50}$ = 30 μM (cortex) | not clear | IC$_{50}$ = 20 μM vs Ro15-4513 (cortex or cerebellum) |
| 53* | ROD.213B (+~10% 213A) | [structure] | N.T. | IC$_{50}$ = 20 μM (cerebellum) IC$_{50}$ > 100 μM (cortex) | not clear | IC$_{50}$~100 μM vs Ro15-4513 |
| 54* | ROD.185 / ROD.207 | [structure] | +351 ± 17% 0.1 μM = +4 ± 10% (78% stimulation by 10 μM and 185 is inhibited by 1 μM flumazenil on α$^1$β$^2$γ$^2$) | IC$_{50}$ = 40 nM (cerebellum) IC$_{50}$ = 150 nM (cortex) | 10 μM = 0% | Displacement of muscimol: 100 μM = 0% IC$_{50}$ vs Ro15-4513 = 200 nM 100 μM of 185 does not influence the GABA inhibition of the TBPS bindings in the brain of rats |

The symbol * indicates a racemic mixture of enantiomers

TABLE 1e

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 62* | ROD.186B | [structure] | +120 ± 20% (0.1 μM = 0%) | 80% (cortex) 85% (cerebellum) 10 μM = 30% (cortex) 10 μM = 40% (cerebellum) | 15% | Muscimol: 100 μM = 0% |
| 63* | ROD.190A | [structure] | +155 ± 47% | 0% | perhaps stimulation | Muscimol: 100 μM = 0% Ro15-4513: 100 μM = 0% |
| 64* | ROD.190B (other diast.) | [structure] | +265 ± 50% | 0% | IC$_{50}$ = 30 μM (cerebellum) IC$_{50}$ > 100 μM (cortex) | Muscimol: 100 μM = 0% Ro15-4513: 100 μM = 0% |

TABLE 1e-continued

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 65* | ROD.212 | | +423% | IC$_{50}$ = 10 μM (cerebellum) 10 μM = 30 μM (cortex) | IC$_{50}$~100 μM | Muscimol: weak stimulation at 100 μM<br>Ro15-4513: IC$_{50}$ = 20 μM |
| 66* | ROD.211 | | +479% | IC$_{50}$ = 50 μM (cerebellum) IC$_{50}$ > 100 μM (cortex) | IC$_{50}$ = 80 μM | Muscimol: weak stimulation at 100 μM<br>Ro15-4513: IC$_{50}$ > 100 μM |

The symbol * indicates a racemic mixture of enantiomers

TABLE 1f

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 67 | ROD.188 | | +579 ± 106% (0.1 μM = 7 ± 5%) | 30% (cortex) 50% (cerebellum) 10 μM = 20% 0.5 μM = 0% | 15% | Muscimol: 5–10% stimulation at 100 μM |
| 68 | ROD.188V1 | | +184 ± 43% | IC$_{50}$ = 20 μM (cerebellum) IC$_{50}$ = 100 μM (cortex) | IC$_{50}$~80 μM | Muscimol: 100 μM = 0% Ro15-4513: IC$_{50}$ = 80 μM |
| 69 | ROD.188V2 | (other enantiomer) | +859 ± 75% (1 μM flumazenil inhibits only 28% of the stimulation by 20 μM of 188V2) | IC$_{50}$ = 10 μM (cerebellum) IC$_{50}$~100 μM (cortex) | IC$_{50}$~40 μM (steep curve) | Muscimol: weak stimulation at 100 μM<br>Ro15-4513: IC$_{50}$ > 100 μM |
| 70* | ROD.220 | | NT | IC$_{50}$ > 100 μM | 0% | Muscimol: weak stimulation at 100 μM in the cortex alone<br>Ro15-4513: IC$_{50}$ > 100 μM |

The symbol * indicates a racemic mixture of enantiomers

TABLE 1g

| Cp No. | Code No. | Structure | % stimulation of the GABA currents (100 μM) | Inhibition of the tritiated ligands | | Other activities |
|---|---|---|---|---|---|---|
| | | | | % Flu (100 μM) | % TBPS (100 μM) | |
| 71* | ROD.221 | [structure: tetrahydroisoquinoline with NSO₂PhOCF₃ and lactone] | NT | IC₅₀ > 100 μM | 0% | Muscimol: weak stimulation at 100 μM in the cortex alone<br>Ro15-4513: IC₅₀ > 100 μM |
| 72* | ROD.222 | [structure: tetrahydroisoquinoline with NSO₂PhOCH₃ and lactone] | NT | 0% | IC₅₀~100 μM (steep curve) | Muscimol: 100 μM = 0%<br>Ro15-4513: 100 μM = 0% |
| 73* | ROD.218 | [structure: tetrahydroisoquinoline with NSO₂PhCH₃ and lactam N-H] | 26 ± 8% | IC₅₀ > 100 μM | 25% | Muscimol: 100 μM = 0%<br>Ro15-4513: IC₅₀ > 100 μM |
| 74* | ROD.219 | other diastereomer | 63 ± 8% | 0% | 40% | Muscimol: 100 μM = 0%<br>Ro15-4513: 100 μM = 0% |
| 55* | ROD.178A | [structure: tetrahydroisoquinoline with NCOCH₂Ph and butenolide] | +33 ± 4% (0.1 μM = 0%) | 95%<br>10 μM = 70% (cortex)<br>80% (cerebellum)<br>0.5 μM = 20% (cortex)<br>30% (cerebellum) | 0% | 100 μM = 0% |

The symbol * indicates a racemic mixture of enantiomers

TABLE 1h

| Cp No. | Code No. | Structure | % stimulation of the GABA currents (100 μM) | Inhibition of the tritiated ligands | | Other activities Displacement of Muscimol |
|---|---|---|---|---|---|---|
| | | | | % Flu (100 μM) | % TBPS (100 μM) | |
| 56* | ROD.178B | [structure: tetrahydroisoquinoline with NCOCH₂Ph and butenolide] | +10 ± 17% (100 μM of 178 blocks the stimulation caused by 20 μM of 164B) | 90% (cortex)<br>85% (cerebellum)<br>10 μM = 70% (cortex)<br>80% (cerebellum)<br>0.5 μM = 20% (cortex)<br>30% (cerebellum) | 10% | 100 μM = 0% |
| 57* | ROD.181A | [structure: tetrahydroisoquinoline with NCO₂Ph and butenolide] | +175 ± 13% (0.1 μM = 0%) | 85% (cortex)<br>90% (cerebellum)<br>10 μM = 75% (cortex)<br>90% (cerebellum)<br>0.5 μM = 25% (cortex)<br>35% (cerebellum) | 20% | 100 μM = 10–20% stimulation<br>10 μM = 0% |

TABLE 1h-continued

| Cp No. | Code No. | Structure | % stimulation of the GABA currents (100 μM) | Inhibition of the tritiated ligands | | Other activities Displacement of Muscimol |
|---|---|---|---|---|---|---|
| | | | | % Flu (100 μM) | % TBPS (100 μM) | |
| 58* | ROD.181B | (structure: tetrahydroisoquinoline with NCO₂Ph and butenolide) | +159 ± 8% (0.1 μM = 0%) | 70% 10 μM = 45% 0.5 μM = 0% | 63% 10 μM = 0% | 100 μM = 0% |
| 60* | ROD.179B | (structure: tetrahydroisoquinoline with NCOPh and butenolide) | +14 ± 13% (0.1 μM = 0%) | 90% 10 μM = 80% (cortex) 90% (cerebellum) 0.5 μM = 25% (cortex) 35% (cerebellum) | 25% | 100 μM = 0% |

The symbol * indicates a racemic mixture of enantiomers

TABLE 1i

| Cp No. | Code No. | Structure | % stimulation of the GABA currents (100 μM) | Inhibition of the tritiated ligands | | Other activities Displacement of Muscimol |
|---|---|---|---|---|---|---|
| | | | | % Flu (100 μM) | % TBPS (100 μM) | |
| 61* | ROD.186A | (structure: tetrahydroisoquinoline with NCOCH₂OPh and butyrolactone) | +232 ± 80% (0.1 μM = 0%) | 95% (10 μM = 90% (cortex) 95% (cerebellum) 0.5 μM = 50% (cortex) 65% (cerebellum) | 35% | 100 μM = 10% |
| 75* | ROD.273 | (structure: dihydroisoquinoline with NCO₂CH₂Ph and butyrolactone) | +148 ± 21% (10 μM) | IC₅₀ = 50 nM (cortex) 26 nM (cerebellum) | | weak stimulation at 100 μM |
| 76* | ROD.279 | (structure: dihydroisoquinoline with NSO₂PhCH₂ and butyrolactone) | +481 ± 116% (10 μM = 97 ± 2%) | 0% | 20% | 20% stimulation at 100 μM |

The symbol * indicates a racemic mixture of enantiomers

The most active compounds are summarized in the following table 2.

TABLE 2

Activity of selected compounds of the invention on the GABA-A receptor

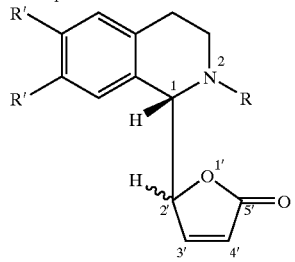

| Compound No. | R | R' | % stimulation of the GABA currents (100 μM) | IC$_{50}$ BZ receptor | IC$_{50}$ TBPS receptor |
|---|---|---|---|---|---|
| (+/−) 48 | CO$_2$CH$_2$Ph | OCH$_3$ | +159 | >100 μM | 0 |
| (+/−) 54 | CO$_2$CH$_2$Ph | H | +351 | 40 nM (ce) | 0 |
|  |  |  |  | 150 nM (co) |  |
| (+/−) 65 | SO$_2$Ph | H | +423 | 10 μM (ce) | ~100 μM |
|  |  |  |  | 30 μM (co) |  |
| (+/−) 66 | SO$_2$Ph-p-Cl | H | +479 | 50 μM (ce) | 80 μM |
|  |  |  |  | >100 μM (co) |  |
| (+/−) 67 | SO$_2$Ph-p-CH$_3$ | H | +579 |  |  |
| (−) 68 | SO$_2$Ph-p-CH$_3$ | H | +184 | 20 μM (ce) | ~80 μM |
|  |  |  |  | 100 μM (co) |  |
| (−) 69 | SO$_2$Ph-p-CH$_3$ | H | +859 | 10 μM (ce) | ~40 μM |
|  |  |  |  | ~100 μM (co) |  |
| Diazepam |  |  | +150 to +300 (1 μM) |  |  | ce = cerebellum
co = whole brain without cerebellum

These examples of compounds and the results obtained with them are indicated without limitation and illustrate the invention.

The conclusions which may be drawn from the study of structure-function are the following:

The most active compounds (that is to say those producing the highest stimulation of the currents produced by GABA) have:

1—a 3',4' unsaturated bond (compare compounds 54 and 50);

2—an oxygen atom at the 1' position rather than a nitrogen atom (compare compounds 67 and 73);

3—the hydrogens at the C-1 and C-2' position have a relative "threo" rather than "erythro" configuration (that is to say of the bicuculline type) (compare compounds 48 and 49);

4—a positive rather than a negative optical rotation in the case of the pure enantiomers of the "threo" diastereoisomers (compare compounds 69 and 68);

5—no alkyl ether substituent on the "A" ring (compare compounds 54 and 48);

6—an aryl carbamate or an aryl sulfonate (that is to say the group R) attached to the nitrogen atom of isoquinoline (compare 48 and 69 with 55).

As regards the mechanism by which these novel compounds stimulate the current produced by GABA, several conclusions may be drawn from the studies of radioactive ligand displacement combined with the electrophysiological results. First of all, none of these compounds binds with the GABA recognition site of the GABA-A receptor. Thus, no, or a very weak displacement of tritiated muscimol is observed in the presence of the compounds of table 2.

Furthermore, in the absence of GABA, no current is produced in the oocyte preparations when any one of these compounds is administered.

The compounds in which the group "R" is a carbamate (for example 54) or another substituent N—C=O (for example 59, 61) appear to stimulate the GABA currents by binding with the benzodiazepine recognition site of the GABA-A receptor in a manner similar to benzodiazepines themselves (diazepam for example). Thus, compound 54 displaces tritiated flunitrazepam with an IC$_{50}$ of 40 nM for the type of receptors found in the cerebellum (BZ1 subtype) and 150 nM for the receptors of the remaining part of the brain (BZ2 receptor subtype). These values compare favorably with those for diazepam, the benzodiazepine prototype, which, nevertheless, demonstrates no selectivity on the subtypes relative to the novel compounds such as compound 54. The potent stimulation of the GABA currents which is produced by the compounds of the 54 type may be prevented to a large extent by the addition of all antagonist of the benzodiazepine receptor in the preparation of oocytes. Thus, 78% of the stimulation produced by 10 μM of compound 54 is prevented by the coadministration of 1 μM flumazenil. This proves that the binding of compound 54 (and of similar analogs) to the benzodiazepine receptor is widely responsible for the stimulation of the GABA currents which is observed.

A remarkable effect is observed with the molecules in which the group R is an arylsulfonyl (for example compounds 65–69). In all cases, the stimulations of the current are much more vigorous than with the analogous carbamate derivative 54. However, the binding affinities with the benzodiazepine receptor are considerably lower. Thus, compound 69 stimulates the GABA current 2.5-fold more strongly than compound 54, and yet shows a binding affinity 250-fold lower for the benzodiazepine receptor. Furthermore, only 28% of the stimulant activity of compound 69 is prevented by flumazenil, an antagonist of BZR. These results clearly indicate that, by far, the largest portion (<70%) of the potent stimulatory activity of GABA produced by the arylsulfonyl derivatives such as compound 69 is due to their interaction with a binding site distinct from those for the benzodiazepines. Although the arylsulfonyl derivatives equally weakly displace TBPS from its binding site on the GABA-A receptor, there is no observable correlation between these binding affinities and the stimulant activities of GABA (table 2).

Other experiments demonstrate that although compound 69 does not produce currents by itself, it can increase the currents produced by pentobarbital. By contrast, the currents produced by GABA which are stimulated by pentobarbital are not further stimulated by compound 69. Furthermore, a mutated receptor incapable of responding to an application of loreclezole shows an unimpaired stimulation of the current by compound 69. Finally, the recombinant receptors of the composition of $\alpha_x\beta_2\gamma_2$ subunits in which x=1, 2, 3, 5, 6 are also tested for the stimulation by compound 69 of the GABA current. The highest stimulation of the current is observed for x=6.

It can therefore be concluded that whereas the carbamate compounds such as 54 represent a novel and a selective subclass of ligands which are agonists of the benzodiazepine receptor, the arylsulfonyl analogs, although demonstrating the same type of GABA stimulating activity as the benzodiazepines, only do so by banding mainly to an as yet noncharacterized site of the GABA-A receptor. These compounds are therefore novel both from a structural point of view and also from the point of view of their novel mode of action. The GABA-stimulating activities of these compounds have a therapeutic benefit, which is demonstrated by the fact that benzodiazepines are widely prescribed. The apparent novel mode of action of the compounds of the present invention suggests that they can possess the beneficial clinical effects of benzodiazepines but with weaker or even no side effects.

It was surprisingly noted that compounds possessing a double bond in the isoquinoline part (compounds 75 and 76) are particularly active.

Furthermore, some of these products demonstrate selectivity for one or other of the numerous GABA-A receptor subtypes. Thus, although compound 32a (table 1b) only weakly stimulates the type $\alpha1\beta2\gamma2$ receptor, this stimulation is greatly increased in cases where the $\alpha1$ subunit is replaced by the $\alpha2$, $\alpha3$, $\alpha5$ or $\alpha6$ subunit. Likewise, compound 73 (table 1g) only weakly stimulates the $\alpha1\beta2\gamma2$ receptor but in the presence of receptors possessing an $\alpha5$ subunit, an inhibition (instead of a stimulation) of the gabaergic currents is observed. This result demonstrates that 73 as well as the other analogous molecules of the present invention have a beneficial effect on memory.

The following examples, given without limitation, illustrate the invention.

METHOD OF SYNTHESIS 2-(tert-Butyldimethylsilyloxy)furan (10, Z=O)

To a freshly distilled solution of 2(5H)-furanone (2.86 g, 34 mmol) in dichloromethane (20 ml), distilled triethylamine (6.6 ml. 47.4 mmol) is added under argon at 0° C. and then rapidly followed by tert-butyldimehylsilyltrifluoromethane sulfonate (8.6 ml, 37.3 mmol) The reaction mixture is allowed to return to room temperature and the stirring is maintained for two hours. The solvent is then removed under reduced pressure and the oily residue is purified by flash chromatography on silica gel (ethyl acetate-heptane, 1:9) in order to thus obtain compound 10 (Z=O) in the form of a slightly colored oil (5.3 g, 79%). The spectroscopic data for this compound ($^1$H and $^{13}$C NMR) are identical to those described in the literature (G. Rassu, Z. Zanardi, L. Battistini, E. Gaetani, G. Casiraghi, J. Med. Chem ., 1997, 40, 168).

(±)-(1R,2'R)- and (±)-(1R,2'S)-1-(2,5-Dihydro-5-oxo-2-furyl)-2-N-benzyloxycarbonyl-6,7-dimethoxy-1,2,3,4-tetrahydroisoquinoline (32a and 32b Respectively)

To a solution of 3,4-dihydro-6,7-dimethoxyisoquinoline (960 mg, 5 mmol) (R. L. Hillard, C. A. Parnell, K. P. C. Vollhardt, Tetrahedron, 1983, 39, 905 and W. M. Whaley, M. Meadow, J. Chem. Soc., 1953, 1067) in anhydrous acetonitrile (10 ml), benzyl chloroformate is slowly added, at 0° C. under argon (0.75 ml, 5.25 mmol). At the end of the addition, the reaction mixture which is dark red in color is allowed to return to room temperature and the stirring is maintained for 15 minutes. A solution of 2-(tert-butyldimethylsilyloxy) furan (10, Z=O) (1 g, 5 mmol) in acetonitrile (1 ml) is then slowly added and the reaction mixture is stirred for 15 minutes at room temperature. The solution is neutralzed with a 5% aqueous solution of sodium hydrogen carbonate (40 ml) and the mixture is extracted with dishloromethane (3×30 ml). The combined organic extracts are dried over MgSO$_4$ and the solvents are removed under reduced pressure, leaving a crude product which is purified by chromatographic column on silica gel (ethyl acetate-heptane, 7:3). $^1$H NMR analysis of the purified product (1.3 g, 63%) indicates the presence of a mixture (3:2) of diastereoisomers. The diaszereoisomers are separated by preparative HPLC on a PrepaPak silica gel column (15–20 $\mu$M) using ethyl acetate-heptane (35:65) as eluent, a flow rate of 50 ml/min and a pressure of 220 psi. The first compound to be eluted is the major three isomer (32a, retention time: 10.3 min) which is crystallized from methanol and has a meleting point of 143° C.

Elemental analysis for C$_{23}$H$_{23}$NO$_6$.0.25H$_2$O: Calculated, %: C, 66.74; H, 5.72; N, 3.38. Found, %: C, 66.73; H, 5.61; N, 3.42.

The minor diastereoisomer (32b) is eluted in 12.1 min and is crystallized from methanol. Melting point: 154° C.

Elemental analysis for C$_{23}$H$_{23}$NO$_6$.0.35H$_2$O: Calculated, %: C, 66.45; H. 5.75; N, 3.37. Found, %: C, 66.47; H, 5.85; N, 3.13.

(±)-Erythro-6,7-dimethoxy-1-(2,3,4,5-tetrahydro-5-oxo-2-furyl)-1,2,3,4-tetrahydroisoquinoline (27a)

A solution of erythro compound 32b (100 mg, 0.24 mmol) in ethanol (8 ml) is hydrogenated at atmospheric pressure for two hours in the presence of 10% palladium on carbon (20 mg). The catalyst is removed by filtration and abundantly washed with ethanol. The combined washings and filtrate are evaporated under reduced pressure and the residue is purified by flash chromatography on silica gel (150 mbar) using dichloromethane-ethanol (95:5) as eluent. Compound 27a is obtained in the form of a solid which is off-white in color (39 mg, 58%) having a melting point of 119° C.

Elemental analysis for C$_{15}$H$_{19}$NO$_4$.0.4H$_2$O: Calculated, %: C, 63.32; H, 7.01; N, 4.92. Found, %: C, 63.24; H, 6.9; N, 4.65.

(±)-Threo-6,7-dimethoxy-1-(2,3,4,5-tetrahydro-5-oxo-2-furyl)-1,2,3,4-tetrahydroisoquinoline (27b)

By Following the same method as for the preparation of compound 27a, the hydrogenation of the threo isomer 32a (100 mg, 0.24 mmol) makes it possible to obtain compound 27b in the form of a yellow oil (39 mg, 58%).

Elemental analysis for $C_{15}H_{19}NO_4.0.6H_2O$: Calculated, %: C, 62.53; H, 7.07; N, 4.86. Found, %: C, 62.33; H, 6.76; N, 4.77.

(±)-(1R,2'R)-2-N-Benzyloxycarbonyl-6,7-dimethoxy-1-(2,3,4,5-tetrahydro-5-oxo-2-furyl)-1,2,3,4-tetrahydroisoquinoline (48)

To a solution of the threo derivative 32a (50 mg, 0.12 mmol) and of nickel(II) chloride hexahydrate (3 mg, 0.012 mmol) in THF (0.8 ml) and methanol (0.2 ml) maintained at 0° C., sodium borohydride (9.25 mg, 0.24 mmol) is added portionwise over 15 minutes. The reaction mixture is allowed to return to room temperature and after stirring for 15 minutes, the mixture is again cooled to 0° C., water is added (5 ml) and the solution is brought to pH 1 by addition of 3N HCl. The mixture is extracted with dichlcromethane (3×5 ml), the combined organic extracts are successively washed with saturated aqueous sodium hydrogen carbonate (5 ml) and saturated aqueous sodium chloride (5 ml) and dried over $MgSO_4$. The solvent is removed under reduced pressure, leaving a residue which is purified, leaving a residue which is purified by chromatographic column on silica gel (ethyl acetate-heptane 7:3) in order to obtain compound 48 in the form of a white amorphous solid (40 mg, 80%).

Elemental analysis for $C_{23}H_{25}NO_6.0.2H_2O$: Calculated, %: C, 66.56; H, 6.17; N, 3.37. Found, %: C, 66.48; H, 5.25; N, 3.32.

(±)-(1R,2'R)-2-N-Benzyloxycarbonyl-1-(2,3,4,5-tetrahydro-5-oxo-2-furyl)-1,2-dihydroisoquinoline (75)

The same method which served for the preparation of compounds 32a and 32b is used, except that the starting material is isoquinoline. The coupling product (only the 1R,2'R isomer is formed) is obtained with a yield of 76%. The double bond of the furanone function is selectively reduced by hydrogenation at one atmosphere in ethyl acetate in the presence of Lindlar catalyst. Compound 75, purified on a silica column, is obtained with a yield of 90%. Its melting point is 109–11° C.

MS(CI)=350 (MH+)

(±)-(1R,2'R)-2-N-Tosyl-1-(2,3,4,5-tetrahydro-5-oxo-2-furyl)-1,2-dihydroisoquinoline (76)

The same method which served for the preparation of compound 75 is used, except that p-toluenesulfonyl chloride is used in place of benzyl chloroformate during the coupling. Compound 76 is obtained with an overall yield of 60% for both stages (coupling and hydrogenation). Its melting point is 147–149° C.

MS(CI): 370 (MM+).

General Method for the N-Acylation and N-Sulfonylation of (±)-Threo-1-(2,3,4,5-tetrahydro-5-oxo-2-furyl)-1,2,3,4-tetrahydroisoquinoline A solution of the desired compound (50 mg, 0.23 mmol) (prepared in the same manner as compound 27a but from compound 50) in anhydrous dichloromethane (2 ml) is treated under argon and at room temperature with triethylamine (39 μl, 0.28 mmol) and the appropriate electrophile RC (1.2 eq) The reaction mixture is stirred overnight, dichloromethane (20 ml) is added and the solution is washed with saturated aqueous sodium hydrogen carbonate (20 ml). The aqueous phase is extracted with dichloromethane (2×10 ml), the organic phases are combined, dried over $MgSO_4$ and the solvent is removed under reduced pressure. The resulting residue is purified by flash chromatography on silica gel (150 mbar) using the solvent system indicated below.

The following compounds are prepared in this manner:

(±)-(1R,2'R)-1-(2,3,4,5-Tetrahydro-5-oxo-2-furyl)-2-N-p-toluenesulfonyl-1,2,3,4-tetrahydroisoquinoline (67) is prepared using p-toluenesulfonyl chloride as electrophile and ethyl acetate-heptane (2:3) as column eluent. Compound 67 is obtained in the form of a white solid with a yield of 85% and a melting point of 140–142° C.

Elemental analysis for $C_{20}H_{21}NSO_4$: Calculated, %: C, 64.67; H, 5.66; N, 3.77; S, 8.63. Found, %: C, 64.53; H, 5.67; N, 4.06; S, 8.51.

(±)-(1R,2'R)-1-(2,3,4,5-Tetrahydro-5-oxo-2-furyl)-2-N-p-chlorobenzenesulfonyl-1,2,3,4-tetrahydroisoquinoline (66) is prepared using p-chlorobenzenesulfonyl chloride as electrophile and ethyl acetate-heptane (2:3) as column eluent. Compound 66 is obtained with a yield of 82% in the form of a white solid having a melting point of 145–147° C.

Elemental analysis for $C_{19}H_{18}NSO_4Cl$: Calculated, %: C, 58.18; H, 4.59; N, 3.57; S, 8.16. Found, %: C, 57.97; H, 4.74; N, 3.41; S, 7.92.

(±)-(1R,2'R)-2-N-Benzenesulfonyl-1-(2,3,4,5-tetrahydro-5-oxo-2-furyl)-1,2,3,4-tetrahydroisoquinoline (65) is prepared using benzenesulfonyl chloride as electrophile and ethyl acetate-heptane (2:3) as column eluent. Compound 65 is obtained with a yield of 81% in the form of a white solid having a melting point of 177–179° C.

Elemental analysis for $C_{19}H_{19}NSO_4.0.4H_2O$: Calculated, %: C, 62.59; H, 5.47; N, 3.84; S, 8.79. Found, %: C, 62.5; H, 5.38; N, 3.92; S, 8.71.

(±)-(1R,2'R)-2-N-Benzyloxycarbonyl-1-(2,3,4,5-tetrahydro-5-oxo-2-furyl)-1,2,3,4-tetrahydroisoquinoline (54) is prepared using benzyl chloroformate as electrophile, a reaction time of 4 hours and ethyl acetate-heptane (1:1) as column eluent. Compound 54 is obtained with a yield of 83% in the form of a colorless oil which solidifies in the long run on standing and having a melting point of 120–122° C.

Elemental analysis for $C_{21}H_{21}NO_4.0.2H_2O$: Calculated, %: C, 71.05; H, 6.08; N, 3.95. Found, %: C, 71.09; H, 6.09; N, 3.76.

What is claimed is:

1. A compound represented by the following general formula:

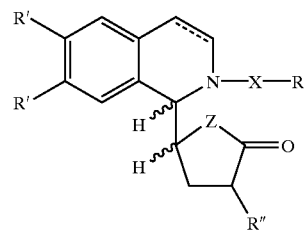

in which:
Z represents a sulfur atom, an oxygen atom, NH, N-alkyl or Nboc, the groups R', which may be identical or different from one another, each represent a hydrogen atom, an OCH₃ group or an OCH₂O group, the group R" represents a hydrogen or a CH₃ group, the group X represents a carbonyl, sulfonyl or CO₂ group and the group R represents an alkyl, aryl, alkenyl or aralkyl group in the form of their racemic mixture or of their optically pure isomers.

2. The compound as claimed in claim 1, wherein Z represents an oxygen atom or Nboc.

3. The compound as claimed in claim 1, wherein Z is an oxygen atom.

4. The compound as claimed in claim 1, wherein the compound is represented by the general formula:

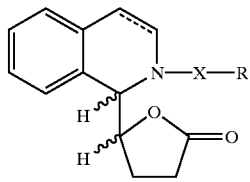

in which:

the group X represents a carbonyl, sulfonyl or CO₂ group and the group R represents an alkyl, aryl, alkenyl or aralkyl group.

5. The compound as claimed in claim 1, wherein the compound is represented by the formula:

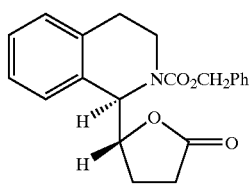

6. The compound as claimed in claim 1, wherein the compound is represented by the formula:

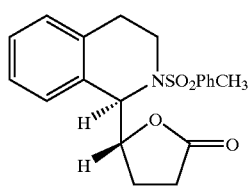

7. A method of preparing a compound, wherein the method comprises:

selectively hydrogenating a compound of the following formula with H₂ in the presence of Pd-C:

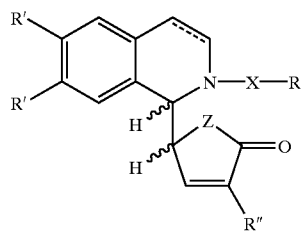

in which:

Z represents a sulfur atom, an oxygen atom, NH, N-alkyl or Nboc the groups R', which may be identical or different from one another, each represent a hydrogen atom, an OCH₃ group or an OCH₂O group, the group R" represents a hydrogen or a CH₃ group, the group X represents a carbonyl, sulfonyl or CO₂ group and the group R represents an alkyl, aryl, alkenyl or aralkyl group, to thereby form a compound as claimed in claim 1.

8. The method of preparation as claimed in claim 7, further comprising a preliminary step of condensing, in the presence of an acylating or sulfonylating agent, a silyl enol ether represented by the general formula:

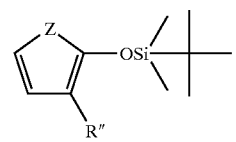

in which:

Z represents a sulfur atom, an oxygen atom, NH, N-alkyl or Nboc and R" represents a hydrogen atom or a CH₃ with a salt of 3,4-dihydroisoquinoline represented by the following general formula:

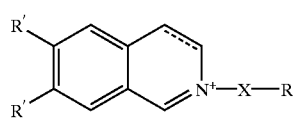

in which:

the groups R', which may be identical or different from one another, each represent a hydrogen atom, an OCH₃ group or an OCH₂O group, the group X represents a carbonyl, sulfonyl or CO₂ group and the group R represents an alkyl, aryl, alkenyl or aralkyl group.

9. A pharmaceutical composition comprising a compound as claimed in any of claims 1 to 6 and an appropriate pharmaceutical carrier.

10. The method of stimulating the activity of γ-aminobutyric acid acting via the GABA-A receptor of the central nervous system comprising administering an effective amount of the compound of claim 1 to a subject.

11. The method of claim 10, wherein the activity of γ-aminobutyric acid acting via the GABA-A receptor is stimulated toward treating a central nervous system disorder comprising epilepsy, anxiety, depression, sleep disorder, memory disorder, panic attack, muscle contraction, pain, dependence on alcohol or on a benzodiazepine or psychotic behavior.

* * * * *

UNITED STATES PATENT AND TRADEMARK OFFICE
CERTIFICATE OF CORRECTION

PATENT NO. : 6,649,626 B1
DATED : November 18, 2003
INVENTOR(S) : Robert Dodd et al.

It is certified that error appears in the above-identified patent and that said Letters Patent is hereby corrected as shown below:

Column 5,
Line 41, change "he" to -- the --.

Column 8,
Line 27, change "benzodlazepines" to -- benzodiazepines --.

Column 10,
Line 46, change "In" to -- in --.
The formula in Scheme 3, change "R=threo-12" to -- threo-12 --.

Column 11,
Line 63, change "Lo" to -- to --.

Column 12,
Line 22, change "he" to -- the --;
Line 55, change "ligated" to -- ligand --.

Column 13,
Table 1a, formual 27a*, delete in its entirety and replace with the following:

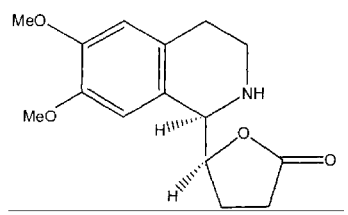

Table 1a, formual 27b*, delete in its entirety and replace with the following:

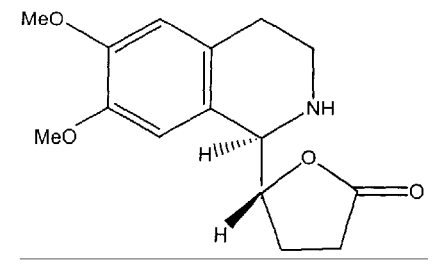

UNITED STATES PATENT AND TRADEMARK OFFICE
CERTIFICATE OF CORRECTION

PATENT NO. : 6,649,626 B1
DATED : November 18, 2003
INVENTOR(S) : Robert Dodd et al.

It is certified that error appears in the above-identified patent and that said Letters Patent is hereby corrected as shown below:

Column 13 (cont'd),
Table 1a, formual 30a*, delete in its entirety and replace with the following:

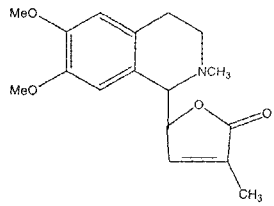

Column 15,
Table 1b, formual 31a*, delete in its entirety and replace with the following:

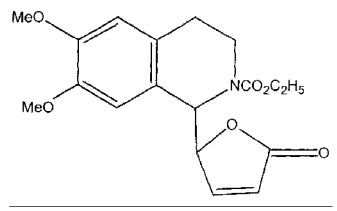

Table 1b, formual 31b*, delete in its entirety and replace with the following:

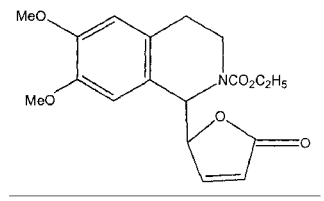

Table 1b, formual 32a*, delete in its entirety and replace with the following:

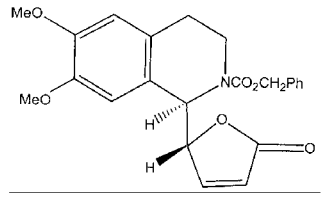

Table 1b, formual 32a*, delete in its entirety and replace with the following:

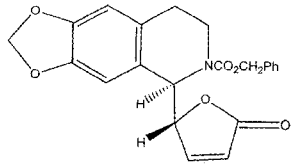

UNITED STATES PATENT AND TRADEMARK OFFICE
CERTIFICATE OF CORRECTION

PATENT NO.   : 6,649,626 B1
DATED        : November 18, 2003
INVENTOR(S)  : Robert Dodd et al.

It is certified that error appears in the above-identified patent and that said Letters Patent is hereby corrected as shown below:

Column 17,
Table 1b, formual 45*, delete in its entirety and replace with the following:

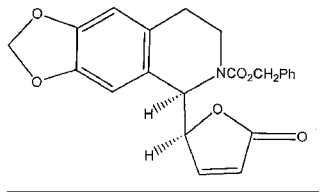

Column 19,
Table 1d, formual 54*, delete in its entirety and replace with the following:

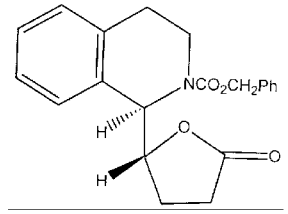

Table 1e, formual 62*, delete in its entirety and replace with the following:

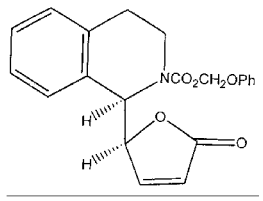

Column 21,
Table 1e, formual 66*, delete in its entirety and replace with the following:

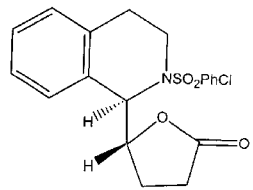

UNITED STATES PATENT AND TRADEMARK OFFICE
CERTIFICATE OF CORRECTION

PATENT NO.    : 6,649,626 B1
DATED         : November 18, 2003
INVENTOR(S)   : Robert Dodd et al.

It is certified that error appears in the above-identified patent and that said Letters Patent is hereby corrected as shown below:

Column 21 (cont'd),
Table 1f, formual 67*, delete in its entirety and replace with the following:

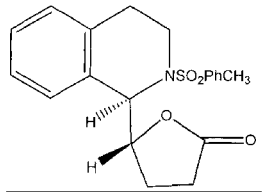

Table 1f, formual 68*, delete in its entirety and replace with the following:

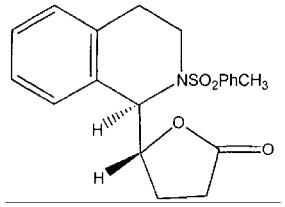

Table 1f, formual 69*, delete in its entirety and replace with the following:

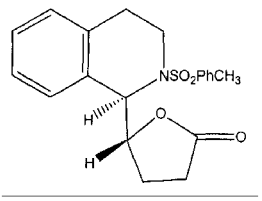

Table 1f, formual 70*, delete in its entirety and replace with the following:

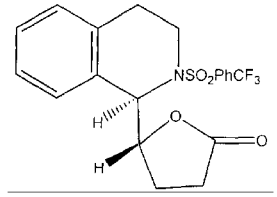

UNITED STATES PATENT AND TRADEMARK OFFICE
CERTIFICATE OF CORRECTION

PATENT NO.    : 6,649,626 B1
DATED         : November 18, 2003
INVENTOR(S)   : Robert Dodd et al.

It is certified that error appears in the above-identified patent and that said Letters Patent is hereby corrected as shown below:

Column 23,
Table 1g, formual 71*, delete in its entirety and replace with the following:

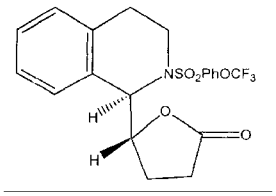

Table 1g, formual 72*, delete in its entirety and replace with the following:

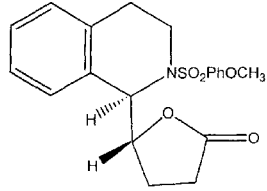

Table 1g, formual 55*, delete in its entirety and replace with the following:

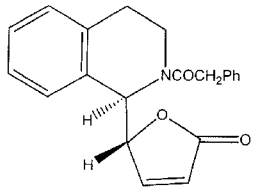

Table 1h, formual 56*, delete in its entirety and replace with the following:

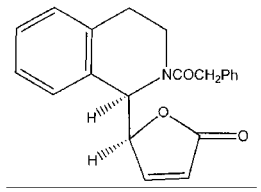

UNITED STATES PATENT AND TRADEMARK OFFICE
CERTIFICATE OF CORRECTION

PATENT NO. : 6,649,626 B1
DATED : November 18, 2003
INVENTOR(S) : Robert Dodd et al.

It is certified that error appears in the above-identified patent and that said Letters Patent is hereby corrected as shown below:

Column 23 (cont'd),
Table 1h, formual 57*, delete in its entirety and replace with the following:

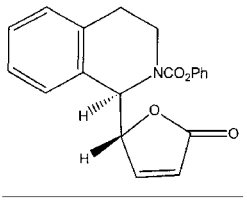

Column 25,
Table 1h, formual 58*, delete in its entirety and replace with the following:

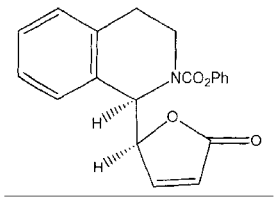

Table 1h, formual 60*, delete in its entirety and replace with the following:

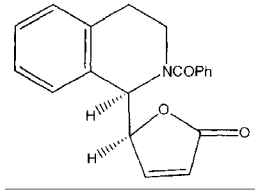

Table 1i, formual 61*, delete in its entirety and replace with the following:

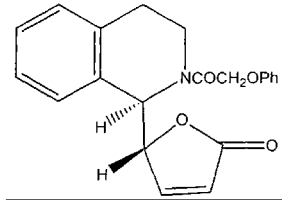

UNITED STATES PATENT AND TRADEMARK OFFICE
CERTIFICATE OF CORRECTION

PATENT NO.   : 6,649,626 B1
DATED        : November 18, 2003
INVENTOR(S)  : Robert Dodd et al.

It is certified that error appears in the above-identified patent and that said Letters Patent is hereby corrected as shown below:

Column 25 (cont'd),
Table 1i, formual 75*, delete in its entirety and replace with the following:

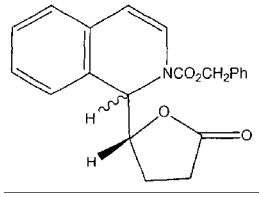

Table 1i, formual 76*, delete in its entirety and replace with the following:

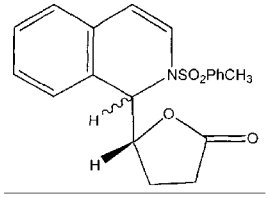

Column 28,
Line 55, change "all" to -- an --.

Column 29,
Line 33, change "banding" to -- binding --.

UNITED STATES PATENT AND TRADEMARK OFFICE
CERTIFICATE OF CORRECTION

PATENT NO. : 6,649,626 B1
DATED : November 18, 2003
INVENTOR(S) : Robert Dodd et al.

It is certified that error appears in the above-identified patent and that said Letters Patent is hereby corrected as shown below:

Column 30,
Line 2, change "butydimehyl" to -- butydimethyl --;
Line 2, change "37.3" to -- 37.5 --;
Line 21, change "chioroformate" to -- chloroformate --;
Line 28, change "neutralzed" to -- neutralized --;
Line 30, change "Dishloromethane" to -- dichloromethane --;
Lines 36 to 37, change "diaszereoisomers" to -- diastereoisomers --;
Line 41, change "three" to -- threo --;
Line 66, change "H, 6.9" to -- H, 6.91 --.

Signed and Sealed this

Seventeenth Day of August, 2004

JON W. DUDAS
*Acting Director of the United States Patent and Trademark Office*